United States Patent
Chumakov et al.

(10) Patent No.: US 8,435,885 B2
(45) Date of Patent: May 7, 2013

(54) METHOD AND SYSTEM FOR EXTRACTING SAMPLES AFTER PATTERNING OF MICROSTRUCTURE DEVICES

(75) Inventors: Dmytro Chumakov, Dresden (DE); Petra Hetzer, Dresden (DE); Matthias Schaller, Moritzburg (DE)

(73) Assignee: GLOBALFOUNDRIES, Inc., Grand Cayman (KY)

(*) Notice: Subject to any disclaimer, the term of this patent is extended or adjusted under 35 U.S.C. 154(b) by 23 days.

(21) Appl. No.: 13/180,143

(22) Filed: Jul. 11, 2011

(65) Prior Publication Data

US 2012/0052601 A1 Mar. 1, 2012

(30) Foreign Application Priority Data

Aug. 31, 2010 (DE) .................... 10 2010 040 069

(51) Int. Cl.
*H01L 21/4763* (2006.01)
(52) U.S. Cl.
USPC ........................................... 438/645
(58) Field of Classification Search ............... 438/645
See application file for complete search history.

(56) References Cited

U.S. PATENT DOCUMENTS

| | | | |
|---|---|---|---|
| 5,004,920 A | 4/1991 | Lee et al. | 250/304 |
| 5,373,365 A | 12/1994 | Brown et al. | 356/430 |
| 5,690,749 A * | 11/1997 | Lee | 134/6 |
| 5,753,563 A | 5/1998 | Guan et al. | 438/476 |
| 5,902,678 A | 5/1999 | Konda et al. | 438/345 |
| 7,528,066 B2 * | 5/2009 | Yang et al. | 438/645 |
| 2002/0071115 A1 * | 6/2002 | Batchelder | 356/237.1 |
| 2003/0000547 A1 * | 1/2003 | Carpenter et al. | 134/1.3 |

FOREIGN PATENT DOCUMENTS

WO WO 91/14935 * 10/1991

OTHER PUBLICATIONS

Translation of Official Communication from German Patent Office for German Patent Application No. 10 2010 040 069.6 dated Jul. 22, 2011.

* cited by examiner

*Primary Examiner* — Charles Garber
*Assistant Examiner* — Andre' C Stevenson
(74) *Attorney, Agent, or Firm* — Williams, Morgan & Amerson, P.C.

(57) ABSTRACT

Analysis of chemical and physical characteristics of polymer species and etch residues caused in critical plasma-assisted etch processes for patterning material layers in semiconductor devices may be accomplished by removing at least a portion of these species on the basis of a probing material layer, which may be lifted-off from the patterned surface. The probing material layer may substantially suppress a chemical modification of the species of interest and may thus allow the examination of the initial status of these species.

21 Claims, 5 Drawing Sheets

METHOD AND SYSTEM FOR EXTRACTING SAMPLES AFTER PATTERNING OF MICROSTRUCTURE DEVICES

BACKGROUND OF THE INVENTION

1. Field of the Invention

Generally, the present disclosure relates to the field of manufacturing of microstructures, such as integrated circuits, and, more particularly, to analysis techniques used for process monitoring and/or process control.

2. Description of the Related Art

In manufacturing microstructures, such as integrated circuits, micromechanical devices, opto-electronic components and the like, device features, such as circuit elements, are typically formed on an appropriate substrate by patterning the surface portions of one or more material layers previously formed on the substrate. Since the dimensions, i.e., the length, width and height, of individual features are steadily decreasing to enhance performance and improve cost-effectiveness, these dimensions have to be maintained within tightly set tolerances in order to guarantee the required functionality of the complete device. Usually, a large number of process steps have to be carried out for completing a microstructure, and, thus, the dimensions of the features during the various manufacturing stages have to be thoroughly monitored to maintain process control and to avoid further cost-intensive process steps owing to process tools that fail to meet the specifications in the various manufacturing stages.

For example, in sophisticated CMOS devices, a very large number of transistors, such as N-channel transistors and P-channel transistors, have to be formed in and above a semiconductor layer, wherein these transistor elements may comprise critical device features, such as gate electrodes and the like, which may have a critical dimension of approximately 50 nm and less in currently available products. In addition to steadily shrinking critical dimensions of the device features, new materials and process strategies may frequently have to be implemented in order to further enhance reliability, performance and cost-effectiveness. Generally, the manufacturing of sophisticated field effect transistors may require new technologies due to limitations increasingly encountered by conventional planar transistor structures based on a gate dielectric material in the form of silicon dioxide, silicon oxynitride and other "conventional" dielectric materials, since these materials may typically result in significantly increased leakage currents, thereby resulting in undue heat generation, which may not be compatible with requirements of many types of semiconductor devices. The limitations of well-established and well-approved dielectric materials in gate electrode structures have fueled new technology approaches, such as non-planar transistor configurations and/or sophisticated gate electrode structures. For instance, the scalability of planar transistor configurations may be significantly expanded by using complex gate electrode structures on the basis of high-k dielectric materials, which are to be understood as materials having a dielectric constant of 10.0 or higher, in combination with metal-containing electrode materials. Consequently, new materials, such as high-k dielectric materials and the like, may have to be implemented into the overall manufacturing flow, thereby requiring appropriate manufacturing techniques for depositing and patterning these materials. For this reason, also any new types of byproducts may be created during the processing of these materials, which may also require a thorough monitoring and investigation with respect to any interactions with other materials and manufacturing processes.

In still other approaches for enhancing transistor performance of complex integrated circuits, strain-inducing mechanisms may be implemented into the overall manufacturing flow for forming field effect transistors since a strained channel region of a silicon-based transistor may provide enhanced transistor performance due to a modified charge carrier mobility caused by the strained silicon-based material. For this purpose, strain-inducing semiconductor alloys, such as silicon/germanium, silicon/carbon and the like, may be incorporated into the active regions in a local manner, thereby selectively inducing a desired type of strain in individual transistor elements. Also in this case, sophisticated patterning and deposition techniques may be required which have to be applied within tightly set process tolerances in order to maintain overall device variability at a low level.

Similarly, after completing the circuit elements in the semiconductor material of complex integrated circuits, a contact level has to be formed, which may be considered as an interface between the circuit elements in the semiconductor material and a complex metallization system, which may be considered as a wiring network for connecting the individual transistor elements and other circuit elements in accordance with the required circuit function. Since, at least in some device regions, a very high density of individual circuit elements may have to be provided, the contact level may have to be formed on the basis of extremely complex deposition and patterning techniques in order to provide appropriate interlayer dielectric materials and patterning the same so as to form contact openings and filling the same with an appropriate metal-containing material. For example, the formation of contact openings in an interlayer dielectric material represents an extremely challenging manufacturing stage for very complex integrated circuits, which may, for instance, comprise densely packed memory areas and the like, since densely spaced contact openings with a high aspect ratio and with critical dimensions of approximately 100 nm and significantly less may have to be formed in a reliable and predictable manner. Consequently, the interaction of the different materials and processes may have a significant influence on the overall production yield in modern semiconductor facilities.

Moreover, typically, very complex metallization systems are required in modern semiconductor devices, wherein the complexity of the metallization system may reside in the fact that a plurality of metallization layers may have to be formed on top of each other, wherein complex material systems may also have to be provided in each of the metallization layers. For example, in modern integrated circuits including a very large number of circuit elements, typically, copper in combination with sophisticated dielectric materials, so-called low-k dielectric materials or ultra low-k (ULK) materials, may be used in order to reduce signal propagation delay in the metallization system. Due to copper's intrinsic characteristics, substantially not to form volatile etch byproducts on the basis of most of the well-established plasma assisted etch chemistries, typically a process technique is applied in which a dielectric material may first be patterned so as to receive corresponding openings, such as trenches and via openings, which are subsequently filled with the copper material by electro-chemical deposition techniques. However, due to the fact that copper may readily diffuse in silicon dioxide, silicon, a plurality of low-k dielectric materials and the like, a reliable confinement of the copper is required, since even minute amounts of copper diffusing to device regions, such as active regions of transistors, may result in a significant change of the overall device characteristics. For this reason, complex barrier material systems may be provided, for instance in the form of tantalum, tantalum nitride, ruthenium, titanium, titanium nitride and the like, which may provide a desired diffusion hindering effect and which may establish the mechanical and chemical integrity of the copper material. Moreover, although copper-based interconnect structures may have a significantly lower electrical resistivity compared to, for instance, aluminum, the reduced dimensions of the interconnect structures may nevertheless result in very high current densities, thereby also requiring strong interfaces between the copper material and the surrounding dielectric material that may have to be provided by the barrier material and corresponding cap materials in order to obtain the required performance with respect to electromigration. Consequently, in the complex manufacturing sequence for forming metallization layers, sensitive dielectric materials may have to be patterned based on appropriate plasma-assisted etch processes, thereby also creating a plurality of etch byproducts, which may have a significant effect on the further processing of the device.

It is well known that, in sophisticated plasma-assisted etch processes, a complex reactive process atmosphere has to be established, which not only includes reactive radicals formed on the basis of fluorine, chlorine and oxygen and the like, but also includes a plurality of molecular species, which may form polymers during the complex interaction of the various species contained in the reactive atmosphere. For example, by adding appropriate hydrogen and carbon-containing process gases, the degree of polymerization may be controlled so as to adjust the general etch behavior during the plasma-assisted process. The polymers may preferably deposit or accumulate at sidewalls of corresponding openings, thereby reducing the lateral etch rate, which may result in an efficient mechanism for controlling the sidewall angle of critical openings. As discussed above, in particular when forming the contact level or sophisticated metallization systems, openings, such as contact openings and via holes, may have to be formed with a high aspect ratio (depth/width) of 5 and significantly higher, wherein a lateral dimension of the openings may be 100 nm or even 50 nm and less in highly sophisticated semiconductor devices. Moreover, in some sophisticated approaches, the polymerization mechanism during the plasma-assisted etch process may even be taken advantage of in reducing the lateral dimension of critical openings, thereby extending the scalability of presently available lithography and etch techniques. That is, upon adding polymerizing gas components, a layer of polymer materials may be formed on sidewalls of critical openings, thereby increasingly forming a layer of polymer material, thereby effectively reducing the lateral width. Due to the complex reaction mechanism, however, a precise knowledge of the composition of the polymer materials and their chemical and physical characteristics may have to be obtained in order to efficiently assess the impact of the polymer material on the semiconductor device. For example, as previously explained, in complex metallization systems, very sensitive dielectric materials, typically provided in the form of low-k dielectrics and porous low-k dielectrics (ULK), are used, at least in critical metallization levels, wherein, however, any additional polymer material may significantly affect any subsequent processes and may also influence the finally obtained electrical performance of the metallization system. One important aspect in forming complex metallization systems is the deposition of an appropriate barrier material prior to depositing the actual fill metal, such as copper, since the barrier material has to provide sufficient adhesion and diffusion blocking capabilities, while at the same time this material may have to provide appropriate interface characteristics in terms of electromigration. Consequently, the presence of any polymer materials which may be generated during the previous complex etch process may significantly influence the deposition of the conductive barrier materials. Moreover, when performing efficient cleaning processes prior to depositing the metal material system, the interaction of the polymer materials with the cleaning chemistry may have to be known in advance in order to appropriately assess the resulting characteristics of the dielectric material. Furthermore, during the plasma-assisted etch processes, the sensitive dielectric materials may typically be damaged since dangling silicon bonds may be present at the exposed surface areas after the plasma-assisted etch process, which may subsequently efficiently react with other components, such as polymer residues and the like, wherein the final surface characteristics may significantly depend on the overall process conditions. Typically, water molecules and the like may adhere to the surface and may finally significantly modify the dielectric characteristics, which in turn may result in an increased dielectric constant of the metallization layer under consideration.

Hence, at various stages during the fabrication of complex semiconductor devices and microstructure devices, the monitoring of surface conditions after performing a complex patterning process on the basis of plasma-assisted etch recipes has become an important aspect. That is, material characteristics on patterned surface areas, such as the presence of polymer materials and etch residues, have to be thoroughly monitored in order to maintain the process output of the various manufacturing stages within the tightly set tolerances. For this reason, a plurality of complex inspection and analysis techniques have been developed in order to characterize the physical and chemical behavior of polymer materials and etch residues formed in patterned semiconductor devices. Since a direct access of the polymer and etch residues on the patterned surface of the semiconductor device may be difficult to achieve, frequently these materials are removed by chemical interaction, for instance by applying appropriate plasma atmospheres or wet chemical etch chemistries in order to analyze the fragments in the plasma atmosphere or in the wet chemical solution. In this case, however, the polymers and the etch residues have to chemically interact in some way with the plasma atmosphere or the wet chemical etch chemistry so that the corresponding analysis results may reflect the material characteristics after the reaction with the plasma or the wet chemistry. Consequently, these analysis techniques are less reliable with respect to providing authentic results of the polymer materials and etch residues, which have initially been formed in the semiconductor device upon forming the patterned surface thereof. Moreover, the "measurement" samples obtained by these conventional process strategies may not allow efficient application of advanced analysis techniques, such as AES (auger electron spectroscopy), SIMS (secondary ion mass spectroscopy), IR (infrared) spectroscopy and the like. Since many of these very efficient analysis techniques may require a specific sample preparation or may require at least specifically designed measurement conditions, which may not be efficiently established on the basis of a plasma or a chemical solution, the surface condition obtained after sophisticated plasma-assisted etch processes may not be efficiently monitored and controlled on the basis of presently available analysis techniques, in particular when surface topographies are considered in which critical dimensions of 50 nm and even less may be encountered.

The present disclosure is directed to various methods that may avoid, or at least reduce, the effects of one or more of the problems identified above.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

Generally, the present disclosure relates to techniques in which etch residues and polymer materials, which are typically produced in these devices after performing sophisticated plasma-assisted etch processes, may be efficiently removed, at least from a portion of the patterned surface, on the basis of a physical interaction with an appropriate probing material substantially without causing any chemical interaction. In some illustrative aspects disclosed herein, the polymer species and the etch residues, which may physically adhere to the probing material, may be subsequently subjected to further analysis, wherein superior sample preparation conditions may be obtained on the basis of the probing material. The probing material may be applied as any appropriate material which may contact the patterned surface of the semiconductor device and may thus physically contact the polymer species and etch residues, however, without actually chemically reacting with these species. The probing material may thus efficiently fill any critical openings, such as openings having lateral dimensions of 100 nm and less, or even 50 nm and less, thereby also efficiently "probing" critical device areas in which the presence of any polymer materials and etch residues may have a strong impact on the overall device characteristics. The probing material layer may then be removed "as a whole." i.e., as a continuous piece of material, which is to be understood that the probing material layer upon removal may form a continuous layer having lateral dimensions that are significantly greater compared to the critical lateral dimensions of the patterned surface. For example, the probing material layer in the form of a continuous piece of material may have lateral dimensions of several hundred micrometers, while, in other cases, significantly larger areas may be covered by the probing material layer. In some cases, the probing material layer may even be applied and removed as a whole from an entire wafer, which may include a plurality of semiconductor dies.

Consequently, after the removal of the probing material layer, a "negative" image of the patterned surface area may be obtained, which may thus enable the establishment of a precise correlation between measurement results obtained on the basis of the probing material layer and the position on the microstructure device. Moreover, the polymer species and etch residues physically adhering to the probing material layer may be effectively analyzed, for instance, by appropriately preparing samples from the probing material layer or by using the probing material layer as a carrier material, without requiring any additional sample preparation except for positioning the probing material layer in an appropriate analysis tool. For example, the actual analysis process may be performed without significant modification of the probing material layer, which comprises the materials of interest adhering thereto, so that many efficient analysis techniques may be applied, such as Fourier transformed infrared spectroscopy (FTIR), in which many chemical characteristics of the species under consideration may be determined in the presence of well-defined measurement conditions. That is, the characteristics of the probing material layer may be determined in advance and may thus act as reference data with respect to the probing material layer having formed thereon the material species of interest. In other cases, the probing material layer may be readily prepared so as to be used in other advanced analysis techniques, such as EAS, SIMS and the like, without requiring the destruction of the microstructure device, thereby resulting in a "non-destructive" analysis strategy for analyzing polymer species and etch residues.

In other cases, the removal of polymer species and etch residues by means of a probing material layer using a physical interaction of the probing material layer and a species of interest may thus provide superior surface conditions for the further processing of the device, while at the same time superior analysis conditions may be established.

One illustrative method disclosed herein relates to analyzing material residues of interest formed on a patterned surface of a microstructure device. The method comprises forming a probing material layer so as to be in physical contact with the patterned surface. The method further comprises removing the probing material layer as a whole from the patterned surface. Additionally, the method comprises performing an analysis process with material residues adhering to the probing material layer.

A further illustrative method disclosed herein comprises forming a plurality of openings in one or more material layers in a semiconductor device, wherein the plurality of openings have at least one lateral dimension of approximately 100 nm or less. Additionally, the method comprises forming a probing material layer above the one or more material layers and within the openings, wherein the probing material layer physically contacts etch residues formed in the plurality of openings. Moreover, a lift-off process is performed so as to remove the probing material layer.

A still further illustrative method disclosed herein relates to the analysis of polymer species and etch residues adhering to a patterned surface of a semiconductor device. The method comprises coating the patterned surface with a probing material that physically contacts at least some of the polymer species and the etch residues. The method further comprises removing at least a portion of the probing material as a continuous piece of material. Furthermore, the method comprises performing an analysis process on the basis of polymer species and etch residues adhering to the continuous piece of material.

BRIEF DESCRIPTION OF THE DRAWINGS

The disclosure may be understood by reference to the following description taken in conjunction with the accompanying drawings, in which like reference numerals identify like elements, and in which.

Figure 1A:
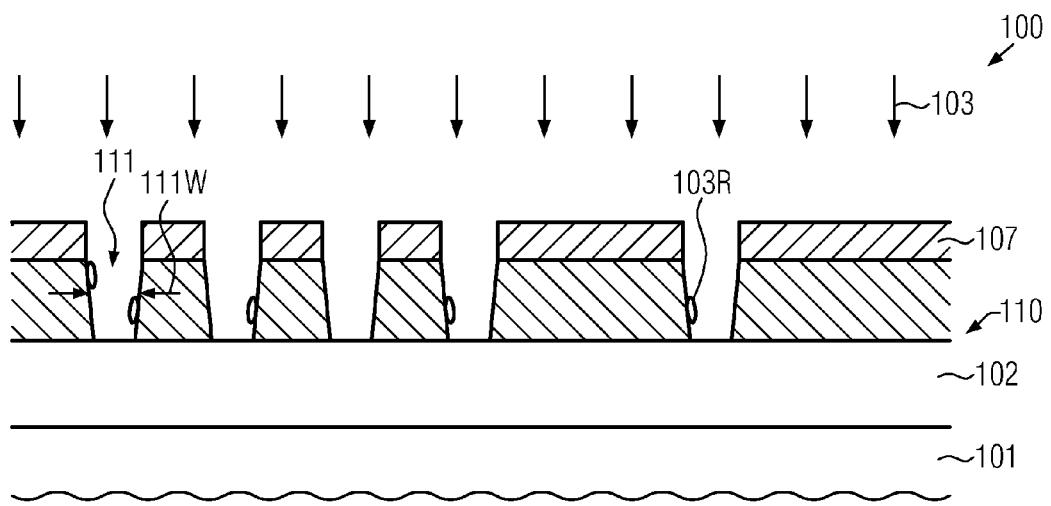
FIG. 1a schematically illustrates a cross-sectional view of a semiconductor device comprising a patterned surface that is formed on the basis of a plasma-assisted etch process, thereby creating polymer species and/or etch residues.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various structures, systems and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

The present disclosure generally provides techniques for removing material residues of interest from a patterned surface of a microstructure device, such as an integrated circuit, during various stages of fabrication thereof without significant chemical interaction so that the material residues, such as polymer species and etch residues, may be analyzed in their initial state, i.e., in a state that substantially reflects the state of these material species on the patterned surface of the microstructure device. To this end, an appropriate "probing" material may be formed on the patterned surface area so as to also fill critical openings formed therein so that corresponding polymer species and etch residues may be contacted by the probing material. The probing material may then be removed, i.e., lifted off or separated from the patterned surface, thereby forming a negative image of the patterned surface, wherein, additionally, at least some of the polymer species and etch residues of interest may adhere to the probing material layer. That is, according to the principles disclosed herein, a negative image of the patterned surface may be formed on the basis of an appropriate fill material, which may also be referred to as probing material, since this material may probe the patterned surface of interest, while at the same time interacting with any etch residues and polymer species, so that at least a portion thereof may adhere upon separating the patterned surface and the probing material. In this manner, the surface condition of the patterned surface may be enhanced, for instance, by removing unwanted etch residues, while at the same time these material species may be accessible by advanced analysis techniques without requiring additional modification of the microstructure device under consideration. In this manner, any advanced analysis technique may be applied in a "non-destructive" manner with respect to the microstructure device under consideration, since, after the separation of the probing material layer and the microstructure device, any desired sample preparation technique may be applied, such as the preparation of cross-sectional samples for transmissive electromicroscopy techniques, preparing appropriate portions of the probing material layer in order to perform any desired analysis technique, such as infrared spectroscopy, AES, SIMS and the like, wherein also the surface topography of the microstructure device itself may be monitored since the probing material layer may represent a negative image thereof.

The probing material may be provided in the form of a low viscous material, such as a polymer material, a resist material and the like, which may be applied so as to form a substantially planar surface, thus reliably filling even critical openings in the patterned surface. To this end, a plurality of optical planarization materials may be readily available, the specific characteristics of which may be adapted by incorporating specific additives in order to, for instance, provide the desired physical interaction capability with the material species and etch residues under consideration. For example, certain components may be added in order to impart electrical conductivity to the probing material, the viscosity may be appropriately adjusted, while in other cases the degree of elasticity and the like may be appropriately adjusted so as to enable an efficient lift-off process, for instance after hardening the probing material when formed on the patterned surface of the microstructure device. The removal of the probing material layer may thus be accomplished as a whole in the sense that at least a portion of the probing material layer may be removed as a continuous piece of material that has an appropriate size for the further handling, for instance, for an appropriate sample preparation for one or more analysis techniques. For example, typically, the term "as a whole" refers to a layer having lateral dimensions of at least 100 μm×100 μm. For example, the probing material layer may be reduced in lateral size to appropriate dimensions by performing any appropriate patterning process, for instance, by using lithography techniques and etch processes, by scanning a laser beam across the probing material layer so as to "vaporize" unwanted portions thereof and the like. Thereafter, a lift-off process may be applied to the remaining portion of the probing material layer. In other cases, the lift-off process may be applied to the layer when still covering the entire wafer, above which a plurality of microstructure devices are formed.

Consequently, after removing at least some of the polymer species and etch residues of interest by means of the probing material layer, the general surface topography may be monitored, and also the characteristics of the species of interest, which adhere to the probing material layer, may be analyzed by applying a plurality of measurement techniques, such as AES, SIMS, FTIR, Raman spectroscopy, TEM (transmissive electron microscopy) and the like, while in other cases the analysis techniques and/or the preparation of appropriate samples may be accomplished by contacting the probing material layer with an appropriate probe, i.e., a nanoprobe and the like.

FIG. 1a schematically illustrates a cross-sectional view of a microstructure device 100 which may comprise a substrate 101, above which may be formed one or more material layers, such as material layers 102, 110, in which device features have to be formed in accordance with the design rules. In some illustrative embodiments, the device 100 may represent a sophisticated semiconductor device in which circuit elements are to be provided on the basis of critical dimensions of 100 nm and less. For example, the layer 102 may comprise a semiconductor material in and above which circuit elements, such as transistors, capacitors, resistors and the like, may be provided, some of which may have critical dimensions, for instance in terms of gate length and the like, of 50 nm and less. For convenience, any such circuit elements are not illustrated in FIG. 1a. It should further be appreciated that the substrate 101 in combination with the one or more material layers 102 may have any appropriate configuration, such as a bulk configuration, a silicon-on-insulator (SOI) configuration and the like. Moreover, the material layer 110 may represent a single material or a system of material layers, depending on the device requirements. In the manufacturing stage shown, the material layer 110 may represent a surface layer which may comprise a plurality of openings 111, thereby forming or defining a patterned surface of the device 100. The openings 111 may have at least one lateral dimension 111W, which may be approximately 100 nm and less. For example, the openings 111 may represent via holes of a metallization layer, contact openings to be formed in a contact level of a semiconductor device, trenches for forming narrow metal lines and the like. As discussed above, the layer 110 may comprise sensitive materials, such as low-k dielectric materials, ULK materials and the like, in which the presence of any polymer species and etch residues, as indicated by 103R, may significantly affect the material characteristics of the material of the layer or layers 110, at least in the vicinity of the openings 111, as is also explained above. In other cases, any other materials may be provided in the layer 110, such as hard mask materials, anti-reflective coating (ARC) materials and the like, which may be used for patterning lower-lying material layers 102, wherein the presence of the polymer species and etch residues 103R may also significantly affect the further processing of the device 100. In other cases, the layer 110 may comprise semiconductor material, which may receive corresponding openings and the like.

The device 100 as illustrated in FIG. 1a may be formed on the basis of any appropriate process strategy. For example, sophisticated circuit elements, such as field effect transistors and the like, may be formed in and above an appropriate semiconductor material, such as a portion of the layer 102, and thereafter any appropriate materials may be deposited in order to passivate the corresponding circuit elements. Thereafter, the one or more material layers 110 may be deposited, for instance by any appropriate deposition technique, wherein, in some cases, one or more of the materials in the layer 110 may be provided in the form of highly stressed materials in order to modify the electrical performance of any semiconductor-based circuit elements which may be formed in the layer 102. To this end, any appropriate thermally activated chemical vapor deposition (CVD), plasma-assisted CVD techniques and the like may be applied. Thereafter, the one or more layers 110 may be patterned, which may be accomplished on the basis of an appropriate etch mask 107, such as a resist mask, a hard mask material and the like. To this end, sophisticated lithography techniques may be applied. Thereafter, a plasma-assisted etch process 103 may be used so as to etch into the layer 110, wherein, as previously discussed, typically, polymer materials and etch residues may be produced, which may adhere to any exposed surface areas of the material 110. That is, the residues 103R may be formed within openings 111. Depending on the etch recipe and the process conditions, as well as the material composition of the layer or layers 110 and 107, different types of polymer materials and etch residues in the form of the residues 103R may be produced and may deposit within the openings 111.

Figure 1B:
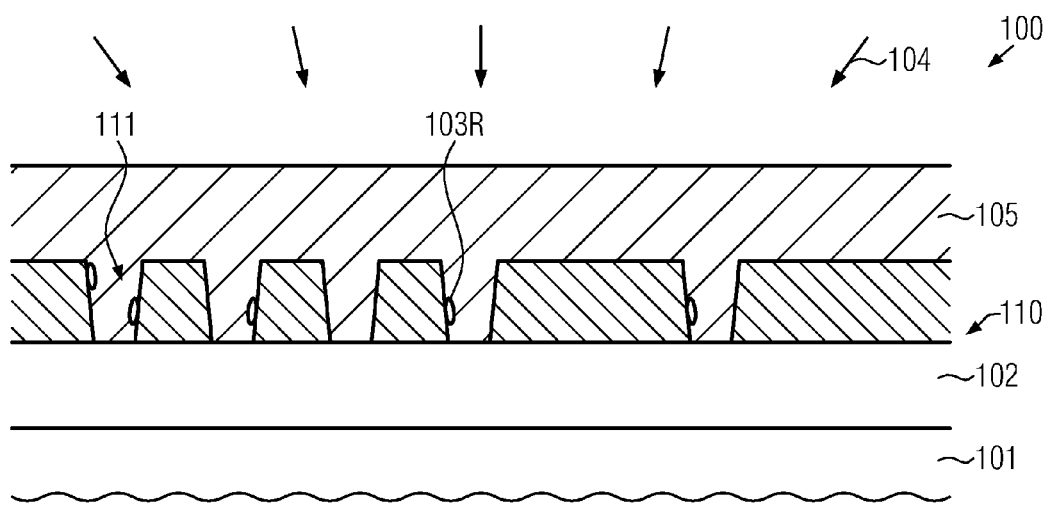
FIG. 1b schematically illustrates the device in a further advanced manufacturing stage in which a probing material layer may be formed so as to be in contact with the patterned surface, according to illustrative embodiments.

FIG. 1b schematically illustrates the device 100 in a further advanced manufacturing stage. As illustrated, the etch mask 107 (FIG. 1a) may be removed on the basis of an appropriate plasma etch process and the like, which in turn may also contribute to the generation or modification of the residues 103R. In other cases, the etch mask 107 of FIG. 1a may be preserved if an analysis of the residues 103R, or generally a removal thereof, is considered appropriate prior to removing the corresponding etch mask. Moreover, a deposition process 104 may be performed in order to form a probing material layer 105 above the layer having the pronounced surface topography, such as the layer 110, thereby also reliably filling the openings 111. The deposition process 104 may comprise well-established spin-on processes in which the material of the layer 105 may be coated onto the layer 110 in a low viscous state, thereby forming a substantially planar surface topography, wherein a thickness of the layer 105 may be selected so as to provide sufficient mechanical stability during the further processing of the device 100. It should be appreciated that a plurality of well-established polymer materials and the like may be deposited in a low viscous state and may subsequently be treated, for instance, by radiation curing, heat treatment and the like, in order to obtain a solid material having specific characteristics, for instance in terms of elasticity. For example, after applying the material 105, the transformation from a liquid state into a solid state may be associated with a certain degree of shrinkage in some illustrative embodiments, for instance by incorporating a specific species that may be removed upon curing the material 105, thereby increasing the physical adhesion of the residues 103R to the material of the layer 105, since, during the shrinkage thereof, the species 103R may be enclosed and thus mechanically attached to the material 105. In other illustrative embodiments, the material characteristics may be selected such that generally the physical adhesion between the species 103R and the material 105 may be greater than the adhesion between the species 103R and the material layer 110. To this end, corresponding experiments and the like may be conducted in order to obtain an appropriate material composition.

Figure 1C:
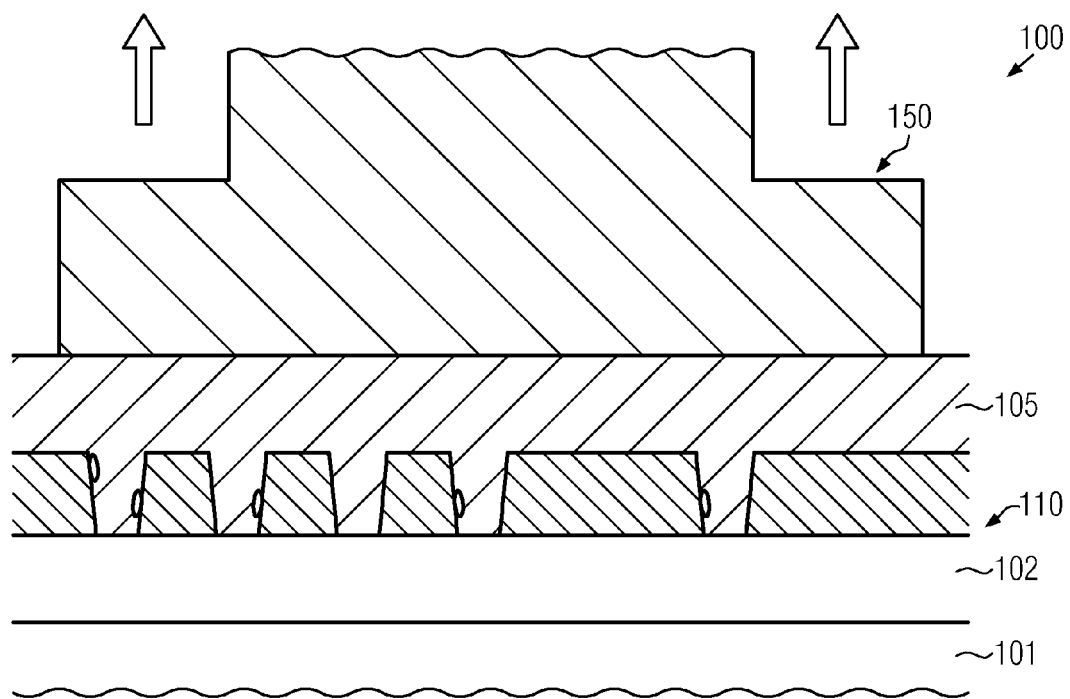
FIG. 1c schematically illustrates the device during a lift-off process in which at least a portion of the probing material layer may be removed as a whole, i.e., as a continuous piece of material, according to illustrative embodiments.

FIG. 1c schematically illustrates the device 100 in a further advanced manufacturing stage. As discussed above, the probing material layer 105 may have been treated so as to be in a solid state, however, nevertheless providing desired mechanical characteristics, for instance in terms of elasticity and the like. Furthermore, a process tool 150 may be brought into contact with the device 100, i.e., the layer 105, in order to perform a lift-off process so as to remove the layer 105 as a whole, i.e., as a continuous piece of material, as is also explained above. To this end, any appropriate process tool may be used, such as are typically used in nano imprint techniques and the like, in which an appropriate stamp may be connected to the material 105 and may be subsequently pulled away so as to mechanically remove the material layer 105. It should be appreciated that the adhesion between the layer 105 and the process tool 150 may be increased by means of any adhesion layer (not shown), by mechanically modifying the layer 105, for instance, providing a "plug and socket-like" configuration so as to appropriately mechanically engage the tool 150 with the layer 105, by means of vacuum and the like.

Figure 1D:
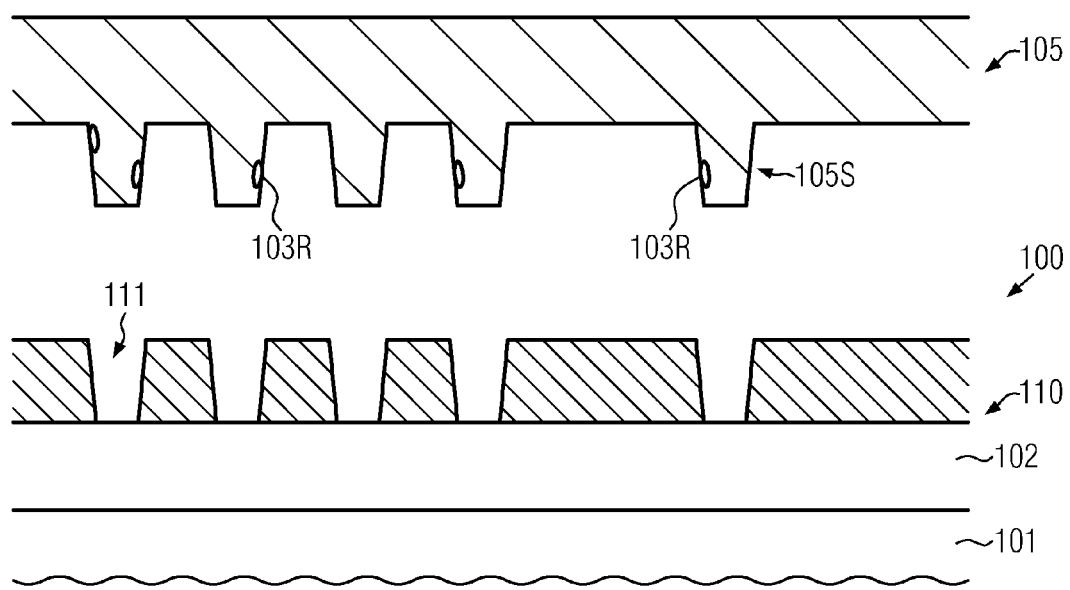
FIG. 1d schematically illustrates a cross-sectional view after separation of the layer and the device, wherein a plurality of polymer species and/or etch residues may adhere to the probing material layer, according to illustrative embodiments.

FIG. 1d schematically illustrates the probing material layer 105 and the device 100 in a separated stage. Consequently, the layer 105 may have a patterned surface 105S, which may thus represent the "negative image" of the surface topography of the layer 110. Furthermore, as shown, at least some of the residues 103R may physically adhere to the patterned surface 105S, wherein, due to the physical interaction between the layer 105 and the residues 103R, any significant modifications may be avoided, in particular a chemical modification may be substantially suppressed upon removing the residues 103R from the device 100. As discussed above, the layer 105 may have a size so as to at least allow an efficient further processing, for instance with respect to performing analysis techniques, which may require a certain degree of sample preparation and the like. In this sense, the probing material layer 105 may be considered as a continuous piece of material, wherein, however, it should be appreciated that certain portions thereof may be "lost" during the separation process due to any mechanical interactions with a process tool, as long as the patterned surface 105S of sufficient lateral size may be preserved.

Figure 1E:
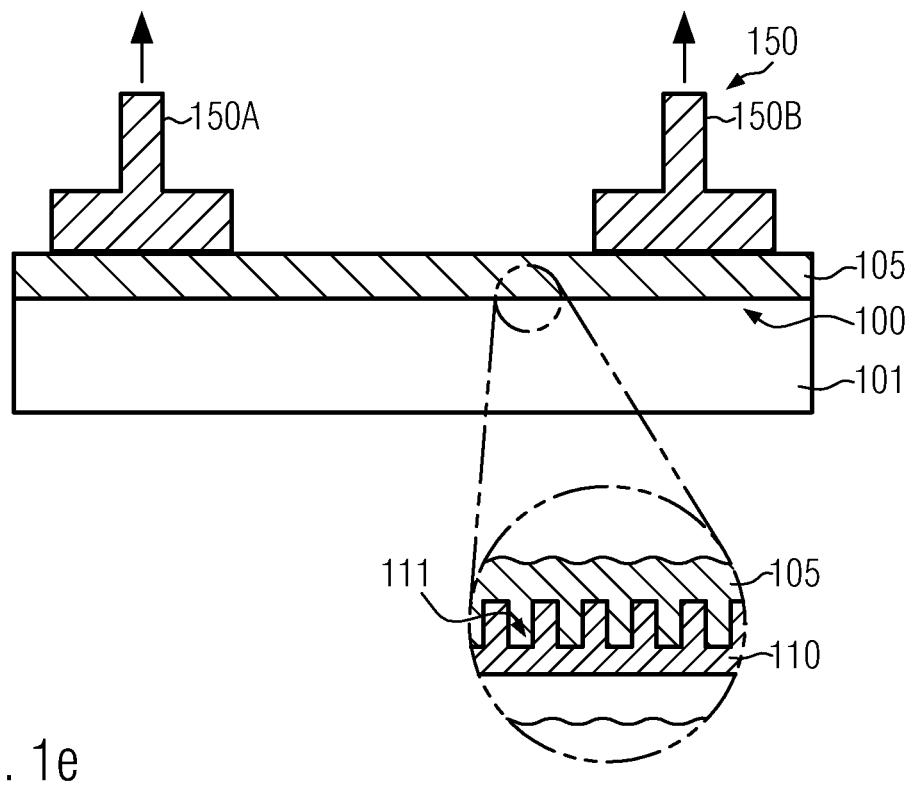
FIGS. 1e and 1f schematically illustrate cross-sectional views of the device and appropriate process tools for separating the probing material layer and the microstructure device, according to illustrative embodiments.

FIG. 1e schematically illustrates the device 100 comprising the probing material layer 105 according to further illustrative embodiments. As shown, the substrate 101 may still be provided in the form of a wafer on which a plurality of the semiconductor or microstructure devices 100 may be provided, for instance in the form of an array of semiconductor dies and the like. In the embodiment shown, the material layer 105 may be applied over the entire wafer 101, wherein the plurality of devices 100 may have the patterned surface in the form of the layer 110, as described above. Furthermore, the lift-off tool 150 may be appropriately configured so as to provide a plurality of stamps 150A, 150B, or any other appropriate means in order to remove the layer 105 as a whole from the wafer 101. For example, a corresponding stamp may be provided that may have substantially the same size and shape as the wafer 101. Consequently, upon removing the layer 105 as a whole, a negative image of the patterned surface of any of the plurality of microstructure devices 100 may be obtained, including any frame regions, scribe lines and the like.

Figure 1F:
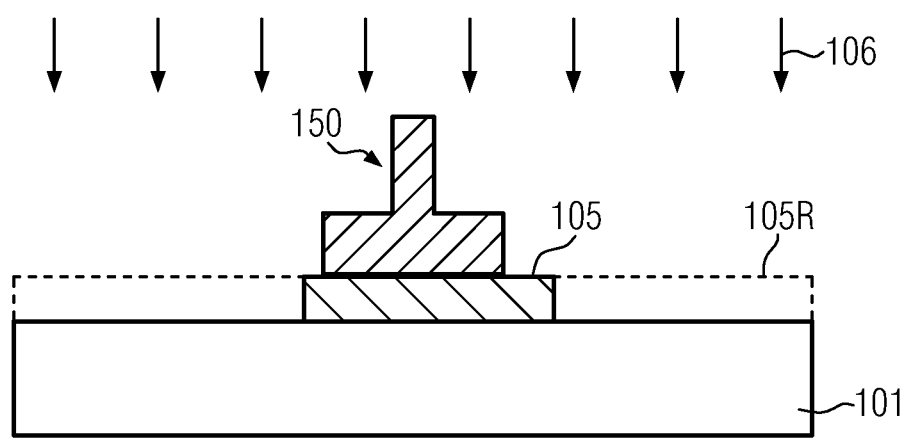

FIG. 1f schematically illustrates the wafer 101 according to further illustrative embodiments in which a portion of the layer 105, indicated as 105R, may be removed prior to performing the lift-off process on the basis of the process tool 150. To this end, any appropriate removal process 106 may be applied, for instance an etch process based on an appropriate etch mask (not shown), while in other cases a laser beam may be scanned across the wafer 101 so as to evaporate the unwanted portion 105R and the like. In this manner, the application of the material 105 may be performed on the basis of well-established manufacturing techniques, such as spin-on techniques and the like, while on the other hand the lift-off process may be restricted to specific areas of the wafer 101, thereby facilitating the removal process. On the other hand, the remaining portion of the layer 105 to be removed by the tool 150 may still have a sufficient lateral size, as discussed above.

Figure 1G:
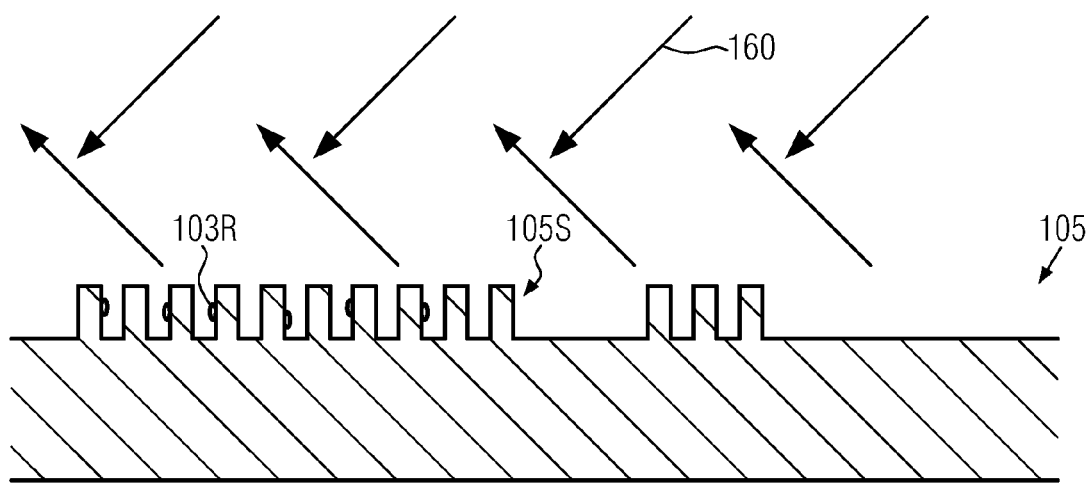
FIG. 1g schematically illustrates a cross-sectional view of the probing material layer, or at least a portion thereof, when subjected to one or more analysis processes, according to illustrative embodiments.

FIG. 1g schematically illustrates the probing material layer 105 when subjected to further processes in order to obtain information regarding the surface topography of the microstructure device 100 (FIG. 1d) and/or the physical and/or chemical characteristics of the residues 103R adhering to the surface 105S. To this end, one or more analysis processes 160 may be performed in order to obtain the desired information. For example, the surface topography of the surface 105S may be determined on the basis of AFM (atomic force microscopy) techniques and the like, by electron microscopy and the like, wherein the sample preparation may not affect the actual microstructure device and the like. In other cases, the one or more analysis processes may include process techniques for obtaining information on the physical and/or chemical characteristics of the species 103R. For example, FTIR techniques may be efficiently applied in which an interference modulated infrared beam may be directed to the surface 105S, or a portion thereof, and wherein, after interaction of the incoming infrared beam with the material of the layer 105, including the species 103R, the reflected beam may be efficiently converted into a spectrum by Fourier transformation that in turn may be analyzed with respect to the chemical characteristics. FTIR is a very time-efficient and effective analysis technique in which chemical characteristics of the species 103R may be detected, for instance, by appropriately determining the influence of the material of the layer 105. For example, reference data may be generated by subjecting the material of the layer 105 to an FTIR analysis so as to obtain the results without any species 103R formed therein.

In other process techniques, an appropriate sample preparation may be accomplished on the basis of the material 105, for instance preparing cross-sectional samples and the like, preparing samples of an appropriate size for AES, SIMS and the like, which may be accomplished on the basis of efficient processes, since the material of the layer 105 may be readily processed due to its superior mechanical characteristics, for instance compared to the mechanical characteristics of a complex layer stack of semiconductor device. Consequently, the one or more analysis processes may be performed as "non-destructive" processes with respect to the initial microstructure device 100 (FIG. 1d).

Figure 1H:
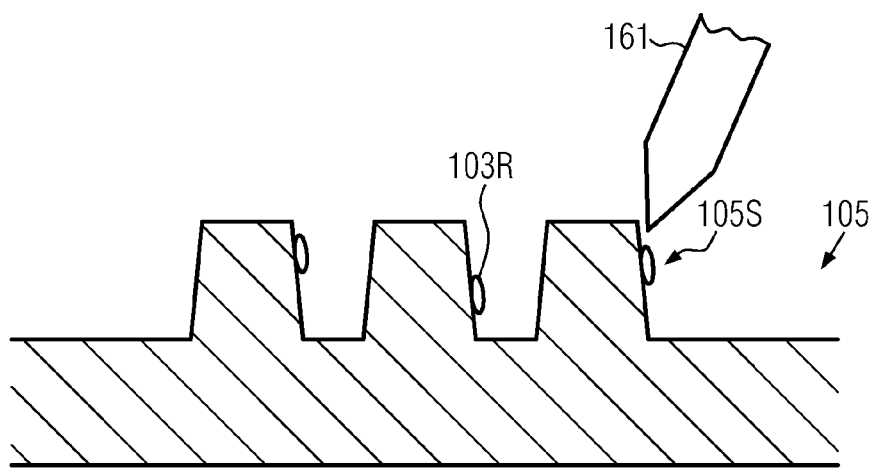
FIG. 1h schematically illustrates a cross-sectional view of a portion of the probing material layer when contacted by a probe for performing analysis processes and/or preparing samples for further analysis, according to illustrative embodiments.

FIG. 1h schematically illustrates a cross-sectional view of the material layer 105 according to further illustrative embodiments wherein the surface 105S may be contacted with an appropriate nano probe 161, for instance to isolate some of the residues 103R. For example, the probe 161 may have specific dimensions so as to allow the contacting of the residues 103R, thereby enabling the further analysis of one or more isolated residues 103R. To this end, the probe 161 may initiate a physical adherence of the residues 103R to the probe 161 without causing a chemical modification in order to not unduly influence the finally obtained measurement results. To this end, the probe 161 may be physically scraped across the surface 105S, while, in other cases, in addition to the mechanical contact, also electrical fields and the like may be applied so as to enhance the adherence of the species 103R to the probe 161.

Figure 1I:
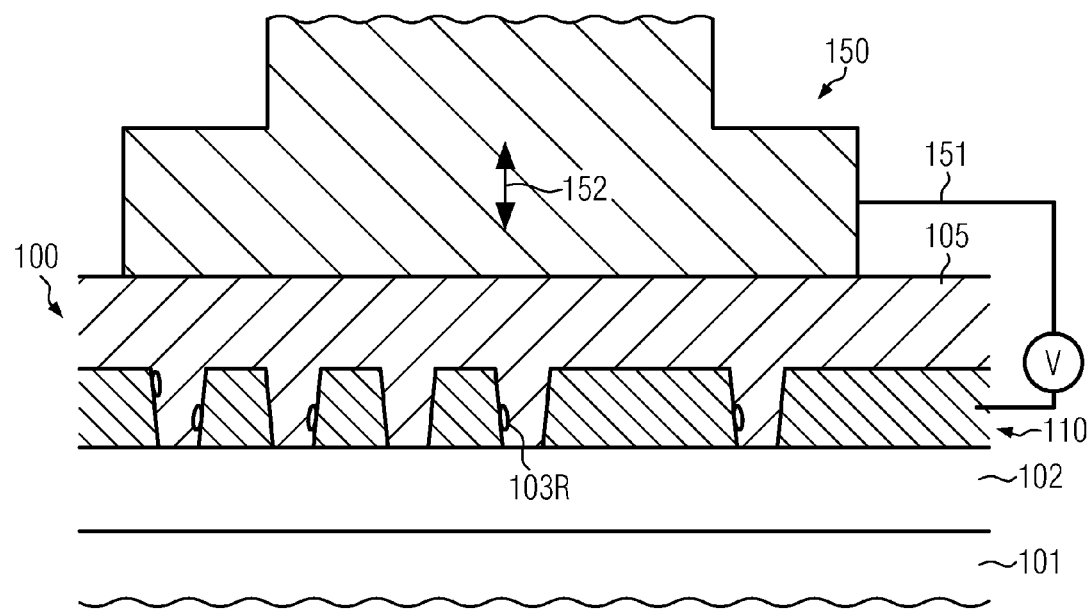
FIG. 1i schematically illustrates a cross-sectional view of the microstructure device having formed thereon the probing material layer, which may be removed by an appropriate lift-off tool while concurrently applying various "stimuli," such as mechanical vibrations, an electrical field and the like, in order to enhance adhesion of the material species of interest to the probing material layer and/or facilitating the separation of the probing material layer from the patterned surface of the microstructure device, according to still further illustrative embodiments.

FIG. 1*i* schematically illustrates the device 100 in combination with the probing material layer 105 according to further illustrative embodiments. As illustrated, upon removing, i.e., separating, the layer 105 from the device 100 by the process tool 150, the removal process may be enhanced and/or the adherence of the species 103R to the layer 105 may be improved by applying an electrical field, for instance by means of a voltage source 151 in combination with an appropriate contact regime. For example, the material 105 may have incorporated therein a conductive species so as to impart a certain degree of conductivity to the layer 105. Thus, the voltage source 151 may be connected to the layer 105, for instance, directly or via the process tool 150, and also the device 100 may be connected to the voltage source 151, thereby applying a certain voltage and thus creating an electric field, which may improve adherence of some sorts of species 103R. In other illustrative embodiments, in addition to or alternatively to the voltage applied across the layer 105, other stimuli may be applied, for instance in the form of mechanical vibrations 152, which may be exerted to the layer 105 and finally to the species 103R, at least during the actual lift-off process. To this end, in some illustrative embodiments, an ultrasonic sound generator (not shown) may be implemented in the tool 150, for instance in the form of a piezoelectric material layer and a corresponding electronic drive circuit in order to mechanically excite the layer 105 and thus the layer 110 including the species 103R. Process parameters, such as energy density of the ultrasonic energy, frequency and the like, may be readily established on the basis of experiments.

As a result, the present disclosure provides techniques for removing polymer species and etch residues from a patterned surface layer from a semiconductor device or microstructure device by applying a material layer that may physically contact the species of interest, thereby enabling efficient removal of these species upon lifting-off the material layer. Consequently, a negative image of the patterned surface layer may be established, which may comprise at least some of the polymer species and etch residues of interest, which may then be subjected to further analysis processes without affecting the actual microstructure device. In this manner, even sophisticated surface topography having openings with 100 nm and significantly less may be monitored. The analysis results of the surface topography and/or of the polymer species and etch residues may be used for enhancing overall process control, such as appropriately selecting process parameters of plasma-assisted etch processes and the like.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of analyzing material residues of interest formed on a patterned surface layer of a microstructure device, the method comprising:
   performing a plasma-assisted etch process to pattern said surface layer, said plasma-assisted etch process generating etch byproducts;
   prior to performing a cleaning process for removing said etch byproducts, forming a probing material layer so as to be in physical contact with said patterned surface layer;
   removing said probing material layer as a whole from said patterned surface layer; and
   performing an analysis process with material residues adhering to said probing material layer.

2. The method of claim 1, wherein said patterned surface layer has a surface topography caused by openings having lateral dimensions of approximately 100 nm or less.

3. The method of claim 1, wherein forming said probing material layer comprises coating said patterned surface layer with a low-viscous material so as to form a substantially planar surface topography and hardening said low-viscous material to form a consistent layer that is removable as a whole.

4. The method of claim 1, wherein removing said probing material layer comprises applying an electric field across said probing material layer so as to increase physical adhesion of said material residues.

5. The method of claim 1, wherein removing said probing material layer comprises applying mechanical vibrations to said microstructure device so as to reduce adhesion of said material residues to said patterned surface layer.

6. The method of claim 5, wherein applying mechanical vibrations comprises mechanically exciting at least a portion of said microstructure device with ultrasonic energy.

7. The method of claim 1, wherein performing said analysis process comprises analyzing said material residues adhering to said probing material layer in the presence of at least a portion of said probing material layer.

8. The method of claim 7, wherein performing said analysis process comprises obtaining reference data from said at least a portion of said probing material layer in the absence of said material residues and analyzing said material residues on the basis of said reference data.

9. The method of claim 1, wherein performing said analysis process comprises removing at least a portion of said material residues from said probing material layer by physically interacting with said probing material layer and analyzing said at least a portion of said material residues.

10. The method of claim 1, wherein performing said analysis process comprises performing at least one of an Auger electron spectroscopy, a secondary ion mass spectroscopy, a Fourier transformed infrared spectroscopy, a Raman spectroscopy and an electron microscopy.

11. The method of claim 1, wherein said probing material layer is formed above a wafer comprising a plurality of said microstructure devices and wherein said probing material layer is removed from said wafer as a whole.

12. The method of claim 1, wherein forming said probing material layer comprises depositing a probing material above a wafer comprising a plurality of said microstructure devices, removing a portion of said probing material so as to preserve said probing material layer above a specified portion of said wafer.

13. A method, comprising:
   forming a plurality of openings in one or more material layers of a semiconductor device, said plurality of openings having at least one lateral dimension of approximately 100 nm or less;
   forming a probing material layer above said one or more material layers and within said openings, said probing material layer physically contacting etch residues formed in said plurality of openings; and performing a lift-off process so as to remove said probing material layer.

14. The method of claim 13, further comprising performing an analysis process so as to assess etch residues physically adhering to said probing material layer.

15. The method of claim 14, wherein performing an analysis process comprises preparing one or more analysis samples from said probing material layer.

16. The method of claim 14, wherein performing an analysis process comprises removing some of said etch residues from said probing material layer by a physical removal process.

17. The method of claim 14, wherein removing at least some of said etch residues from said probing material layer comprises initiating an interaction between a probe and said etch residues by at least one of applying a mechanical pressure, scratching a portion of said probing material layer, applying an electric field, controlling a temperature of said probe and said probing material layer, applying radiation energy and generating mechanical vibrations.

18. A method of analyzing polymer species and etch residues adhering to a patterned surface layer of a semiconductor device, the method comprising:
    coating said patterned surface with a probing material, said probing material physically contacting at least some of said polymer species and etch residues;
    removing at least a portion of said probing material as a continuous piece of material; and
    performing an analysis process on the basis of polymer species and etch residues adhering to said continuous piece of material.

19. The method of claim 18, wherein said patterned surface layer comprises openings having a lateral dimension of 50 nm or less.

20. A method, comprising:
    forming a patterned surface layer of a microstructure device, said patterned surface layer comprising a plurality of openings having lateral opening sizes of approximately 100 nm or less, wherein forming said patterned surface layer comprises forming material residues thereon;
    forming a probing material layer so as to be in physical contact with said patterned surface layer having said material residues thereon;
    removing said probing material layer as a whole from said patterned surface layer; and
    performing an analysis process to analyze at least a portion of said material residues adhering to said probing material layer.

21. A method, comprising:
    forming a patterned surface layer of a microstructure device, wherein forming said patterned surface layer comprises forming material residues thereon;
    forming a probing material layer so as to be in physical contact with said patterned surface layer having said material residues thereon;
    removing said probing material layer as a whole from said patterned surface layer, wherein removing said probing material layer comprises applying an electric field across said probing material layer so as to increase physical adhesion of said material residues to said probing layer; and
    performing an analysis process to analyze at least a portion of said material residues adhering to said probing material layer.

* * * * *